United States Patent [19]
Zuest et al.

[11] Patent Number: 5,630,717
[45] Date of Patent: May 20, 1997

[54] DENTAL IMPLANT BAR SYSTEM AND METHOD

[75] Inventors: Max Zuest, San Diego; Paul Zuest, Poway, both of Calif.

[73] Assignee: Zest Anchors, Inc., Escondido, Calif.

[21] Appl. No.: 432,086

[22] Filed: May 1, 1995

[51] Int. Cl.$^6$ ................................................ A61C 13/225
[52] U.S. Cl. ............................................................ 433/172
[58] Field of Search ................................... 433/172, 173, 433/174, 175, 176, 177, 199.1, 201.1, 213, 181, 182

[56] References Cited

U.S. PATENT DOCUMENTS

| | | | |
|---|---|---|---|
| 4,906,191 | 3/1990 | Söderberg | 433/213 |
| 4,931,016 | 6/1990 | Sillard | 433/172 |
| 5,007,833 | 4/1991 | Barbone | 433/172 |
| 5,052,928 | 10/1991 | Andersson | 433/172 |
| 5,219,286 | 6/1993 | Hader | 433/172 |
| 5,234,341 | 8/1993 | Johansen | 433/172 |
| 5,246,368 | 9/1993 | Sillard | 433/172 |
| 5,286,196 | 2/1994 | Brajnovic et al. | 433/172 |
| 5,362,235 | 11/1994 | Daftary | 433/172 |
| 5,417,570 | 5/1995 | Zuest et al. | 433/177 |
| 5,419,700 | 5/1995 | Sillard | 433/172 |
| 5,427,906 | 6/1995 | Hansen | 433/173 |
| 5,476,382 | 12/1995 | Daftary | 433/172 |
| 5,480,304 | 1/1996 | Nardi | 433/172 |

FOREIGN PATENT DOCUMENTS 0305075  3/1989  European Pat. Off. .

OTHER PUBLICATIONS

Miller, Dennis, "Laboratory Fabrication of an Implant Supported and Retained Milled Bar Overdenture," *Trends and Techniques in the Contemporary Dental Laboratory*, vol. 10, No. 9, Nov. 1993, pp. 27–31.

Lewis, Steve, "Implant-Retained Overdentures," *Compend. Contin. Educ. Dent.* vol., XIV, No. 10., pp. 1270–1283.

Astra Tech Implants Brochure, "Prosthodontic Treatment –Overdenture," pp. 4, 6–7.

*Primary Examiner*—Cary E. O'Connor
*Attorney, Agent, or Firm*—Brown, Martin, Haller & McClain

[57] ABSTRACT

An implant bar attachment system and method includes an elongate bar for extending between at least two implant sites and at least two fastener devices at opposite ends of the bar for securing the bar to the respective implants. The bar has socket formations for snap engagement with the heads of respective male members secured to an overlying denture. At least some of the socket formations are provided in the heads of female fastener devices which extend through bores in the bar at respective implant sites for connection to an implant or implant abutment, so that the denture attachment point is coaxial with the implant.

35 Claims, 3 Drawing Sheets

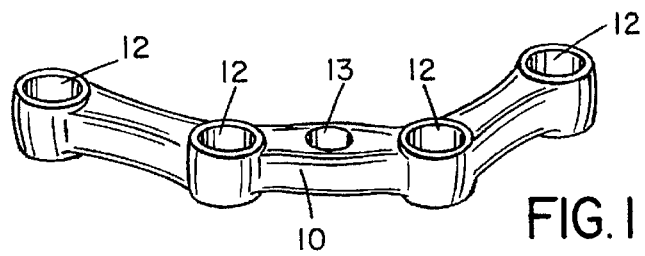
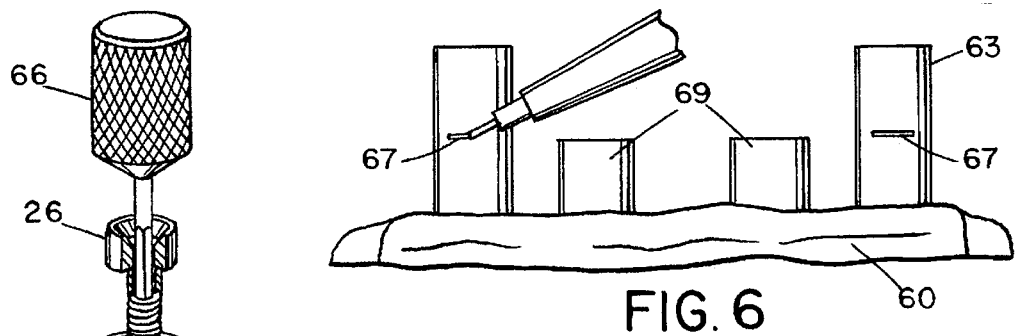
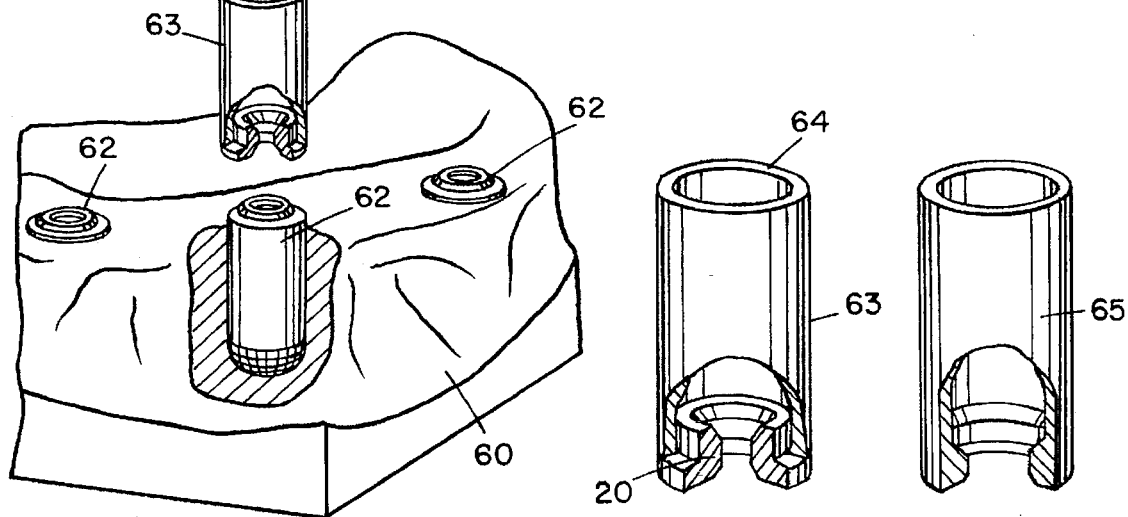
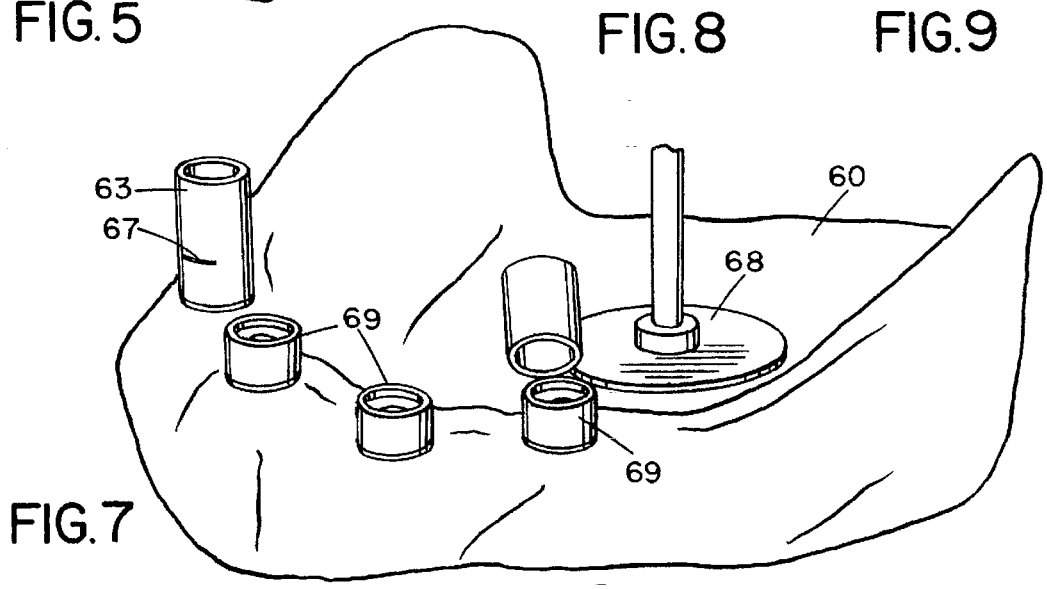

DENTAL IMPLANT BAR SYSTEM AND METHOD

CROSS-REFERENCES TO RELATED APPLICATIONS

The present invention is related to application Ser. No. 08/176,597 of the same Applicants, filed Jan. 3, 1994, now U.S. Pat. No. 5,417,570.

BACKGROUND OF THE INVENTION

This invention relates to bar attachment systems for attaching implants to dentures.

Implants in the jawbone often act as anchor points for dental prosthetic devices such as crowns, bridges, and partial and full dentures. In upper dentures, and often in lower dentures, several implants are splinted together by a bar, and the bar is connected in turn to the denture. This provides better support for the denture and distributes load more evenly. This is particularly important in the upper jaw where the bone is less dense. Use of a bar also retains the denture attachment fixtures parallel to one another, making insertion and removal easier. Conventional bars typically attach to the implants by means of screws at the ends of the bar. The bar has upwardly projecting balls or horizontal bars for snap engagement with a cooperating socket in the denture.

One problem with existing bar attachments is that they have a relatively high profile, due to the balls or bars which project up above the bar. This makes the bar uncomfortable to the patient when the denture is removed for cleaning or overnight. It also takes up room in providing the socket space in the denture itself.

Another problem is the lateral torque produced due to the offset between the denture attachment points and the implant attachment points. This produces a cantilever effect which may tend to loosen the implant. Additionally, where implants are located close together, as is normal due to the fact that implants can normally only be placed in anterior regions of the mouth to reduce the risk of contact with the nerve, there is little space left for providing the denture attachment balls or bars. Conventional bars also cannot be secured over highly divergent implants. Proper fitting is another problem with existing bar systems, which often need to be repeatedly cut and re-soldered due to poor initial fitting.

SUMMARY OF THE INVENTION

It is an object of the present invention to provide a new and improved implant bar attachment system and method.

According to one aspect of the present invention, a dental implant bar system is provided which comprises an elongate bar for extending between at least two dental implants, at least two fastener devices at opposite ends of the bar for connecting the bar to the respective implants, at least two socket formations in the bar, and at least two male members, each male member having a first end for securing to a dental appliance and a second end for releasable snap engagement in a respective one of the socket formations.

Preferably, the bar has at least two through bores, each through bore being aligned with a respective implant, and the fastener devices each have a head for engaging in one of the through bores and a shaft for projecting out of the through bore for engagement in a respective implant. The socket formations are preferably provided at the implant attachment sites, and may comprise suitable sockets formed in the heads of the fastener devices. The sockets have a low profile within the bar, providing a lower root to crown or denture leverage factor The bar has a low profile, since the denture is attached via male members secured to the denture which project down into low profile sockets within the bar itself. Thus, there is no need for any parts projecting above the level of the bar. Additionally, the denture attachment is positioned directly over the implant, avoiding cantilever forces. Functional forces are thereby directed along the longitudinal axis of the implant, providing safer, axial loading.

The fastener devices may be secured directly to an implant, where the gum level is relatively low, or may be secured to a gingival cuff or abutment, where the implant is spaced a substantial distance below the gum level. The abutments will be provided in a range of different cuff heights.

Preferably, the bar has a plurality of precision machined, annular seats secured to the undersurface of the bar at each through bore site, each seat having a lower surface shaped for close mating engagement with the upper surface of an implant or abutment member. The remainder of the bar is preferably of cast metal.

According to another aspect of the present invention, a method of attaching a denture to at least two implants is provided, which comprises the steps of: securing a bar to extend between the implants by means of fastener devices at the respective implant sites, the bar having at least two socket formations at the respective implant sites, securing at least two male members to a denture at locations corresponding to the respective implant sites, and snap engaging the projecting ends of the male members into the socket formations below the surface of the bar so as to releasably secure the denture to the bar.

The attachment between the denture and the bar is located within the bar itself, rather than spaced above the level of the bar as in prior bar systems. This takes up considerably less space in the denture itself, and in the patient's mouth. This low profile bar system takes up very little height above the cast bar and provides a connection point low within the bar.

According to another aspect of the invention, a method of making a bar for splinting together two or more implants and securing to a denture is provided, which comprises taking an impression of the implant locations in a patient's jaw, fabricating a model of the patient's jaw using the impression, including implant analogs at the implant locations, securing a castable plastic sleeve to each implant analog, securing a castable plastic bar section between each adjacent pair of plastic sleeves to form a plastic framework, shaping the plastic framework to the desired jaw contour, fitting the plastic bar framework in the patient's jaw by fastening each sleeve to a respective implant and cutting and reshaping the plastic bar if necessary for a correct fit, and using the resultant fitted plastic bar framework to cast a matching metal bar.

With this method, a perfect fit of the cast metal bar is ensured without further cutting and soldering being necessary on fitting to the patient. The plastic bar pattern can be cut and adjusted to fit the patient's mouth much more readily than a cast metal bar, eliminating cut and solder corrections. Preferably, the plastic pattern includes machined metal seats at the lower end of each castable sleeve wherever the bar meets an implant abutment, so that the same precision fit may be evaluated both before and after casting.

The dental implant bar attachment system and method of this invention is easier to fit to a patient's mouth. The bar itself is of a much lower profile than previous bars, and the attachments of the bar to the denture are aligned with the implant axes, producing safer, axial loading forces rather than cantilever or torque forces which may damage implants. The system is compatible with existing implant designs and may be attached directly to an implant or to an implant abutment. The bar is preferably curved to follow the ridge of a patient's jaw, allowing support directly under the teeth of a denture where mastication forces are greatest.

BRIEF DESCRIPTION OF THE DRAWINGS

The present invention will be better understood from the following detailed description of a preferred embodiment of the invention, taken in conjunction with the accompanying drawings, in which like reference numerals refer to like parts, and in which:

FIG. 1 illustrates the finished casting of a typical configuration of a bar for an implant bar attachment system according to a preferred embodiment of the invention;

FIG. 5 shows the attachment of a positioning sleeve to an implant analog in a model;

FIG. 6 is a front view of the sleeve arrangement on a model, with the cutoff markings;

FIG. 7 illustrates the cutting off of the sleeves to the required height;

FIG. 8 is an enlarged perspective view of a sleeve with a metal insert;

FIG. 9 is a similar view without a metal insert;

DESCRIPTION OF THE PREFERRED EMBODIMENT

FIG. 1 of the drawings illustrates an elongate, cast metal bar 10 according to a preferred embodiment of the present invention which may be used to splint together a plurality of implants embedded in a patient's jaw and may also be releasably secured to a dental prosthetic device such as a full or partial denture. By using a bar to splint together several implants, rather than anchoring a denture directly to the implants, a stronger attachment is provided since the rigid bar connects the implants together, rather than the denture itself connecting the implants.

As illustrated in FIG. 1, the bar has a plurality of through bores 12, each through bore being aligned with the position of an implant in the patient's jaw to which the bar is to be attached. Thus, bar 10 must be custom-made to fit each patient, and FIG. 1 illustrates only one exemplary case. The bar may be made with a greater or lesser number of implant bores, dependent on implant locations in the patient's jaw, but will always have at least two implant attachment bores 12 at opposite ends of the bar. Any suitable non-toxic metal may be used, as is conventional in dental implant restorations, such as precious and semiprecious alloys of gold, palladium or silver. The bar may also include one or more upwardly or outwardly facing sockets 13.

Figure 2:
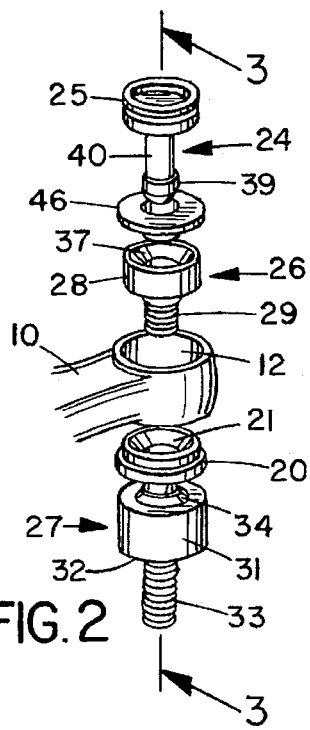
FIG. 2 is an exploded view of a bar attachment at one end of the bar.
Figure 3:
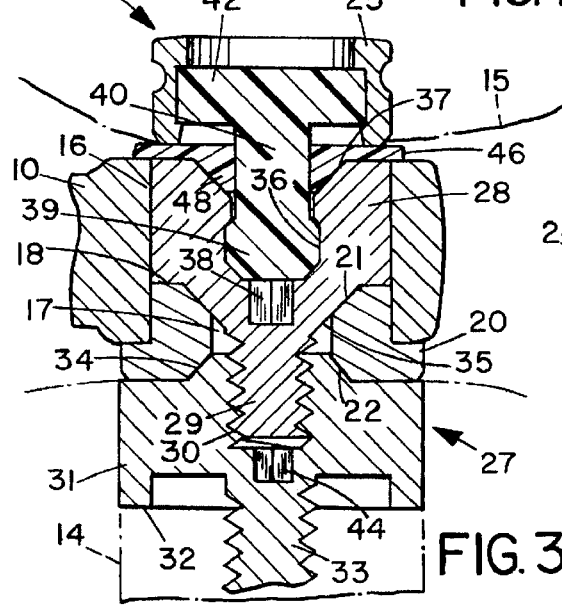
FIG. 3 is an enlarged sectional view taken on line 3—3 of FIG. 2, with the components assembled.
Figure 4:
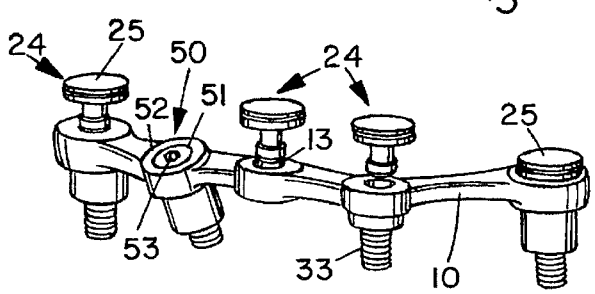
FIG. 4 illustrates another bar configuration with other types of attachments.

At each through bore location, the bar is attached to an implant 14 and also to an overlying denture 15 by means of an attachment assembly, as illustrated in more detail in FIGS. 2–4. FIGS. 2 and 3 illustrate the components of an attachment assembly at one implant attachment bar site, where the implant is secured to the bar and the bar is coaxially secured to the denture. Each through bore 12 through the bar is of stepped diameter, having a larger diameter outer end portion 16 and a smaller diameter inner or lower end portion 17, with an outwardly facing step or seat 18 between the different diameter portions. Preferably, the lower end portion of each bore is formed by a separate, machined metal ring or annular seat member 20 which is cast in position to the remainder of the bar, as described in more detail below in connection with FIGS. 5–16. The annular seat member is of precious metal such as gold. The seat member 20 preferably has a tapered rim portion 21 surrounding the upper end of bore portion 17, and a tapered rim portion 22 surrounding the lower end of bore portion 17, as illustrated in FIG. 3.

The attachment assembly basically comprises a male part 24 having a cap 25 at one end, a female part 26, and an optional cuff or abutment member 27. Female part 26 comprises a fastener screw which has a head 28 seated in the larger diameter portion of the bore in mating engagement with seat or step 18 and a threaded shaft 29 projecting through the lower end portion of the bore. Shaft 29 is secured in a threaded bore 30 in the abutment member 27, which in turn is secured to implant 14, in the embodiment illustrated in FIGS. 2 and 3. However, where the gum thickness above the implant is relatively small, the shaft 29 may be threaded directly into the threaded bore of the implant. The diameter of shaft 29 and the dimensions of the threads on the shaft will be dependent on the type of implant or implant abutment member 27. Implant abutment member 27 comprises a cylindrical cuff portion 31 with a downwardly depending annular rim 32, and a central, threaded shaft 33 for threaded engagement in an implant bore. An annular boss with a tapered rim 34 surrounds the upper end opening of bore 30, for mating engagement with the correspondingly tapered rim portion at the lower end of seat member 20. Abutment members 27 will be provided in a range of different cuff heights to accommodate different gum thicknesses, and with different thread parameters and shaft diameters for attachment to different types of implant. FIG. 4 illustrates abutment members of different cuff heights attached at the various through bores on the bar.

The lower face of the head 28 of screw 26 is shaped for close mating engagement with seat 18, and has an annular, downwardly facing, tapered portion 35 for close mating engagement with the correspondingly tapered inner portion 21 of step 18. Head 28 has an upwardly or outwardly facing female socket 36 with an outwardly facing, tapered opening 37. A hexagonal recess 38 for receiving a hex tool for tightening the screw is provided at the lower end of socket 36. A similar hexagonal recess 44 is provided at the lower end of bore 30 in abutment member 27. The socket 36 is shaped and dimensioned for releasable snap engagement with a correspondingly shaped head 39 at one end of plastic or nylon male member 24. Male member 24 has an elongate shaft 40 with head 39 at one end and an enlarged head 42 at the opposite end for permanent engagement in metal cap 25 which in turn is secured in a recess in dental appliance or prosthesis 15. Cap 25 is a relatively short, annular member of gold-plated metal, which will take up relatively little room in a denture. Head 42 is a snap lock fit in cap 25, so that it cannot be removed after engagement with the cap. Head 39 is releasably snap engaged in socket 36, so that it can be repeatedly snapped into and out of the socket 36 as desired. A retainer or centering ring 46 of resilient material is slidably mounted on shaft 40. Ring 46 comprises a flat annular flange with a central opening fitting over shaft 40 and a downwardly facing, tapered boss or abutment 48 for engagement in the tapered opening 37 of socket 36. Ring 46 is used only for centering purposes during fabrication of a denture or prosthesis, and will be removed after a properly centered denture has been fabricated.

The cap, male member and screw or female member for securing a denture through a bar and to an implant are similar to the denture attachment system as described in our co-pending application Ser. No. 08/176,597 filed Jan. 3, 1994, the contents of which are incorporated herein by reference. However, the cap 25 and head 42 of the male are shorter than the version described in that application, although head 39 and socket 36 are of equivalent shape. It will be understood that, although this is the preferred structure for attaching the denture to both the bar and the implant, other snap-engaging parts may alternatively be used. For example, a spherical ball and socket joint may be used, with a spherical or part-spherical socket in the screw head and a corresponding spherical or part-spherical male member for engagement in the socket, the male member being secured in any suitable manner to the denture.

When the head 39 is snapped into socket 36, relative rotation between the two parts is permitted about the axis of shaft 40. The 360° ball and socket rotation of the attachment allows freedom in the design of the implant bar, since the prosthesis is not limited to only one plane of movement. Thus, the bar can be placed anywhere along the dental ridge to provide support directly under the denture teeth. The 360° rotatability permits the bar to be curved to follow the curvature of a patient's jaw, allowing support to be provided directly under the denture teeth, where mastication forces are greatest. Additionally, the ball and socket joint permits a swivelling motion of up to around 7° to 8°.

An attachment assembly as illustrated in FIGS. 2 and 3 may be used at any non-divergent implant location, i.e. any implant which is parallel with other implants or with the desired path of denture insertion, or any implant which has a divergence of less than 10° from such an orientation. If one or more implants is divergent at an angle greater than or equal to 10°, the bar is simply secured to the divergent implant by means of a bar retaining screw 50, as illustrated in FIG. 4. Screw 50 is identical to female member 26 except that it does not have a socket 36 and tapered opening 37. Instead, the screw head has an upper end face 52 which is flat and has a hex recess 53 for receiving a suitable tightening tool. Screw 50 has a threaded shaft identical to shaft 29 for extending through bore portion 17 to threadably engage either a bore 30 in an implant abutment 27 or, where the gum is relatively thin, to threadably engage directly in the bore of a divergent implant.

Where the spacing between adjacent implants is too great for good denture support, or where there are one or more divergent implants, the bar 10 will be provided with a female socket 13 at an appropriate location, typically adjacent any divergent implant. Female socket 13 will be identical to the socket 36 and opening 37 in female screw member 26, so that the head 39 of a male member 24 may also be snap engaged in a female socket 13. One or more female sockets 13 may be provided in the bar as necessary.

It can be seen from FIGS. 1 and 4 that the implant bar 10 of this invention has a very low profile and will not project very far above the gum level, making it more comfortable when the denture is removed for cleaning purposes or overnight. The female socket member forms the attachment socket for the male member which secures the denture to the bar, and simultaneously attaches the bar to the underlying implant. This provides a denture attachment which is coaxial with each non-divergent implant, avoiding cantilever forces which may damage or loosen implants.

A basic implant bar system will comprise an elongate bar extending between two spaced implants and having through bores at its opposite ends, and an implant attachment assembly extending through each through bore to secure the denture to the bar and secure the bar coaxially to the implant. Additional through bores may be provided for attachment to other implants between the two end implants. Divergent through bores may be provided for attaching the bar to any divergent implants via a bar retaining screw 50, as illustrated in FIG. 4. Additionally, if necessary, female sockets 13 may be provided in the bar at locations between implants, to provide additional anchoring points for male members secured to a denture. The female socket members and retainer screws may be secured directly to the implant, where the gum height is less than 2 mm, or may be secured to an intervening abutment member 27, for gum heights greater than 2 mm.

In a preferred embodiment of the invention, the cast bar with female socket member will extend around 3 mm above the abutment member, or the implant itself where the female member is secured directly to the implant. The male and cap extends an additional 1.5 to 2 mm above the top of the cast bar. Thus, the bar attachment system measures just 4.5 to 5 mm from the top of the gum or tissue to the top of the low profile male member and cap. The male member is preferably of resilient material such as nylon and provides shock absorption, reducing impact load on the attached implants.

Preferably, the female member or fastener 26 and the bar retaining screw 50 are provided with heads of at least two different heights, allowing the bar to be cast in different, corresponding profile heights depending on the crest height at the implant sites. The upper face of head 28 of female part 26 and the upper face 52 of screw head 51, where used, will be flush with the upper surface of the bar. It will be understood that bars may be used to splint implants together in either the upper or lower jaw, and most commonly in the upper jaw. Thus, the term "upper" in the foregoing description refers to the outermost face of the respective part, i.e. the farthest away from the gum, while the term "lower" refers to the face closest to the gum, regardless of whether the bar is in the upper or lower jaw.

Preferably, heads 28 and 51 are provided in heights of 2 mm and 3 mm. Where implant sites in a patient's jaw are of different heights, as determined by a bite plane or similar leveling device, a 2 mm attachment is used at the or each highest crestal implant site, and a 3 mm attachment at the lower sites in order to create a level upper or outer bar surface. Where the differential between implant sites is greater than this, an implant abutment member having a greater height may be used to fulfil the vertical requirement in order to produce a level bar surface.

A preferred procedure for fabricating a custom bar 10 for securing to implants in a patient's jaw and to an overlying denture or other dental prosthesis via the above attachment system will now be described in more detail with reference to FIGS. 5–16. Normally, the bar will be used to splint together 3 or 4 implants in the upper or lower jaw. Use of bars is most common in the upper jaw where the bone is more spongy and the implants are therefore more susceptible to loosening or damage. Once implants have been placed and have undergone osseointegration with the patient's jawbone, some initial measurements must be made in the patient's jaw. The gingival thickness at each implant location must be measured from the crestal rim of the implant body to the crest of the gingiva. If the tissue thickness exceeds 2 mm at any site, an appropriate abutment member 27 is secured to the implant to extend the implant fixture to the tissue level. The abutment member is selected to match the implant brand and diameter being used, and with a cuff height closest to the measured tissue thickness. An appropriate hex driver tool is used to thread the abutment member into the implant. The bar will be attached to the abutment member at any implant sites having a tissue thickness of greater than 2 mm, and directly to the implant at any sites where the tissue thickness is less than 2 mm.

The divergence, if any, of each implant is determined. If any implant has a divergence of greater than 10° to the other implants, or to the path of insertion of a removable prosthesis, a bar retaining screw must be used to secure the bar to the implant at the divergent implant site. If it is determined that additional retention will be necessary for the prosthesis, in view of the divergent implant or implants which will not provide an attachment site for the prosthesis, one or more sockets will be provided directly in the bar itself adjacent the or each divergent implant.

Also, as noted above, the differential height between implant sites is calculated in order to determine the appropriate height female members or fastener screws to use at each site, as discussed above. Once these measurements have been made, an impression post is secured to each implant at each site where the tissue thickness is less than 2 mm, and an abutment impression post is secured to each of the abutment members at sites where the tissue thickness is greater than 2 mm. At this point, impression material is injected around the impression posts so as to fill the impression tray. The impression tray is removed and the impression posts are unscrewed from the implants and implant abutments. Caps are placed over each of the implants and implant abutments in the patient's jaw while the laboratory fabrication procedures are being performed, as is conventional.

The impression is used to transfer the implant sites into a stone or soft tissue model 60. Implant or implant abutment analogs 62 are secured to each of the impression posts in the impression, and the model is poured. The resultant model is separated from the impression. FIG. 5 illustrates part of such a model 60 including implant or implant abutment analogs 62 which duplicate the implant sites in the patient's jaw. Model 60 is used to fabricate a plastic bar pattern as illustrated in FIGS. 5–14.

A castable plastic sleeve 63 is first secured to each of the analogs 62 using a female fastener 26 or a retaining screw 50, depending on the divergence of the implant analog. Two alternative types of castable plastic sleeve are illustrated in FIGS. 8 and 9. The preferred castable sleeve 63, as illustrated in FIG. 8, comprises a plastic tube 64 having an annular gold seat member 20 secured by adhesive or the like to the lower end of the tube 64. Alternatively, a castable sleeve 65 may be made entirely of castable plastic material, as illustrated in FIG. 9. The internal diameter of sleeve 63 or the upper end of sleeve 65 corresponds to the desired diameter of the through bore 18 in the fabricated bar 10.

Sleeve 63 is secured to the respective implant analog 62 using a female fastener 26 at all non-divergent implant sites, as illustrated in FIG. 5. Castable sleeves 63 will be provided with different seats for matching different brands of implant and implant diameters, as well as implant abutments. The appropriate sleeve 63 is therefore selected, and a hex driver tool 66 is engaged in the hex recess 38 at the inner end of the socket in the female fastener in order to secure the sleeve and female fastener to the implant or abutment analog 62.

Each castable sleeve 63 is then marked with a line 67 at a level just above the upper face of the female attachment screw or fastener 23, as illustrated in FIG. 6. As noted above, female fasteners of different head heights may be used in order to accommodate differential implant site crest heights. The female screw or fastener 26 is then removed, and the castable sleeve 63 is cut off at the marked line 67 using a cutting disc 68. The top of the sleeve is smoothed off to remove any burs. The resultant cut plastic sleeves 69 are then re-secured using the appropriate attachment screws 23 or 50.

Figure 10:
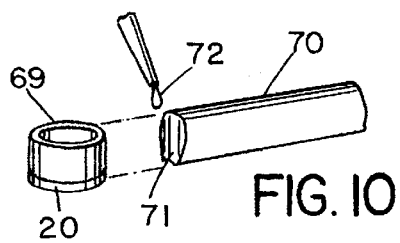
FIG. 10 illustrates the adhesive attachment of a bar section to a sleeve.
Figure 11:
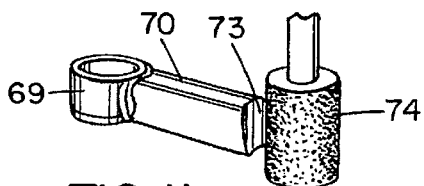
FIG. 11 illustrates shaping of the bar section to the required length for attachment to another sleeve.
Figure 12:
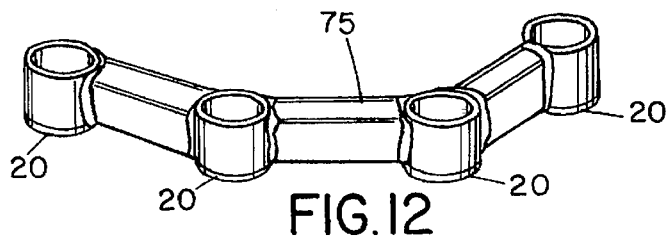
FIG. 12 is a perspective view of a completed rough bar model.

A length of plastic castable bar 70 is then secured between each adjacent pair of plastic sleeves 69, as illustrated in FIGS. 10–12. Two different types of plastic bars are provided, one of which is thicker than the other. The thicker plastic castable bar is used where the resultant cast bar is to include a socket 13 for receiving a male member offset from an implant site, for example where there are one or more divergent implants. Each castable plastic bar 70 has one concave end 71 for fitting against the mesial side of one castable plastic sleeve 69, as illustrated in FIG. 10. The end 71 is suitably bonded to the sleeve 69 using a suitable quick-setting adhesive 72 such as Poly-Zap. The bar is then marked at the appropriate length for fitting between the first sleeve and the next adjacent sleeve, and cut to this length. The cut end 73 is then machined with a diamond bar end bur 74 to form a concave surface into the cut end, as illustrated in FIG. 11. The machined end 73 is then adhered to the distal side of the adjoining castable plastic sleeve. The procedure is repeated until all of the castable sleeves 69 are joined together by a castable plastic bar section 70, forming a castable plastic bar pattern 75 as illustrated in FIG. 12. A thicker bar section is used in any location where a socket is to be provided in the bar between two implant sites. The plastic sleeves and bar sections are of any suitable castable plastic material for use in investment casting, such as polycarbonate.

Figure 13:
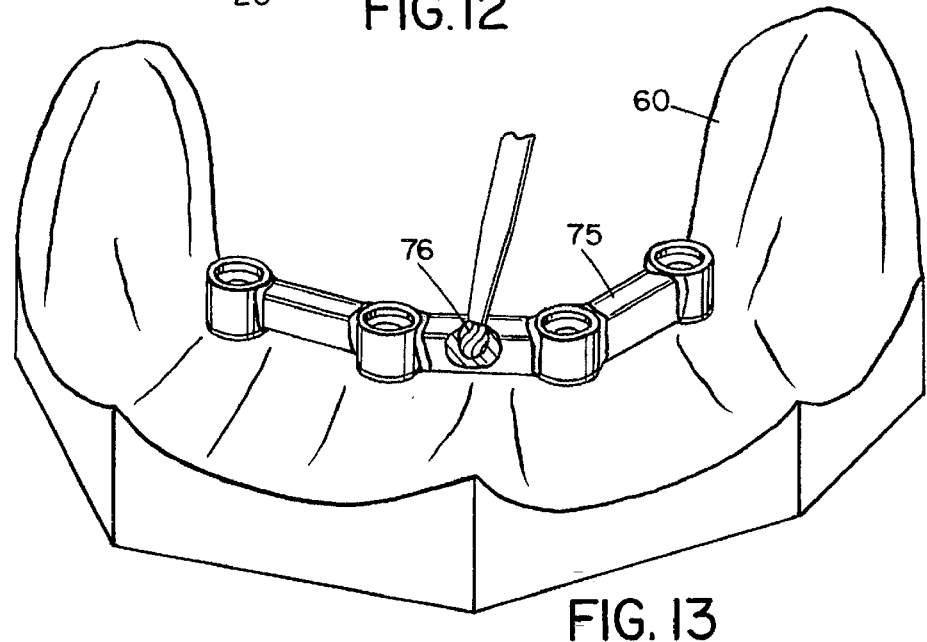
FIG. 13 illustrates attachment of the bar to an alignment model.
Figure 14:
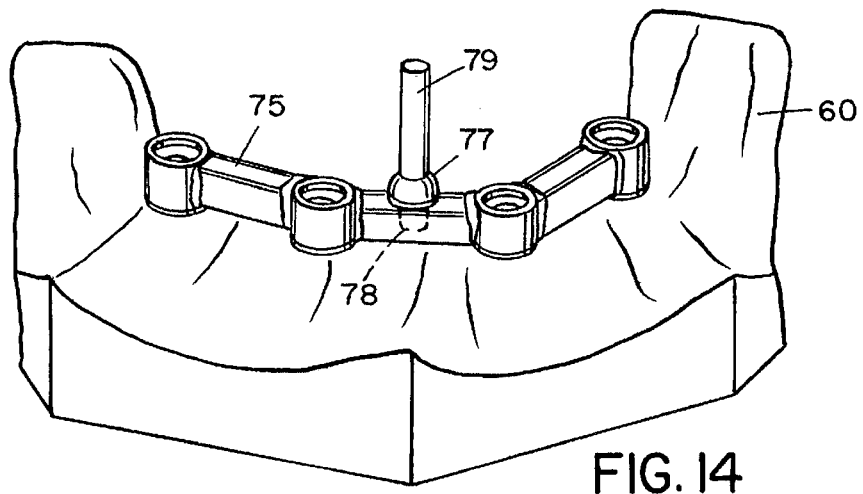
FIG. 14 is a similar view with a casting bar attached.

A round bur 76 is used to create a recess in the plastic bar pattern 75 at any location where a female socket is to be provided, as illustrated in FIG. 13. A cast-to-bar female 77 is then secured in the resultant space by a suitable adhesive, as illustrated in FIG. 14. The female includes a female socket part 78 of metal, such as stainless steel, which is suitably bonded in the prepared recess in the bar pattern, and a projecting carbon rod 79. The shape of the socket portion 78 which is embedded in the bar pattern 75 will correspond to the desired socket shape for snap engagement with the head 39 of a male member 24. The projecting rod 79 is oriented parallel with the sleeves and the desired path of prosthesis insertion, as illustrated.

When the castable plastic bar pattern is completed, it is screwed onto the master cast model for a final fit check, before delivering it to the dental office for an intra-oral fitting to the patient. The sturdy, polycarbonate bar pattern 75 with precision machined gold seats 20 allows an intraoral fit verification before final casting of the bar. Any adjustments necessary for a proper fit can be made readily in the plastic bar pattern, virtually eliminating the need for any cut and solder corrections after casting.

The plastic bar pattern and attachment screws are delivered to the dental office for fitting to the patient. The bar pattern 75 is placed in position in the patient's mouth and the attachment females 26 or screws 50 are used to secure the pattern to the respective implants or abutments, using a hex driver tool. The fit of the pattern on the implants is verified. If an adjustment is necessary, the plastic bar may be simply cut while it is seated on the implants, and bonded together in the desired, altered position. Since the modified plastic bar pattern will no longer fit properly on the laboratory model, it is necessary in this case to take another impression and fabricate another model from the impression in the laboratory. An impression male may be secured to each female member 23 in order to check that the attachments are all parallel.

Figure 15:
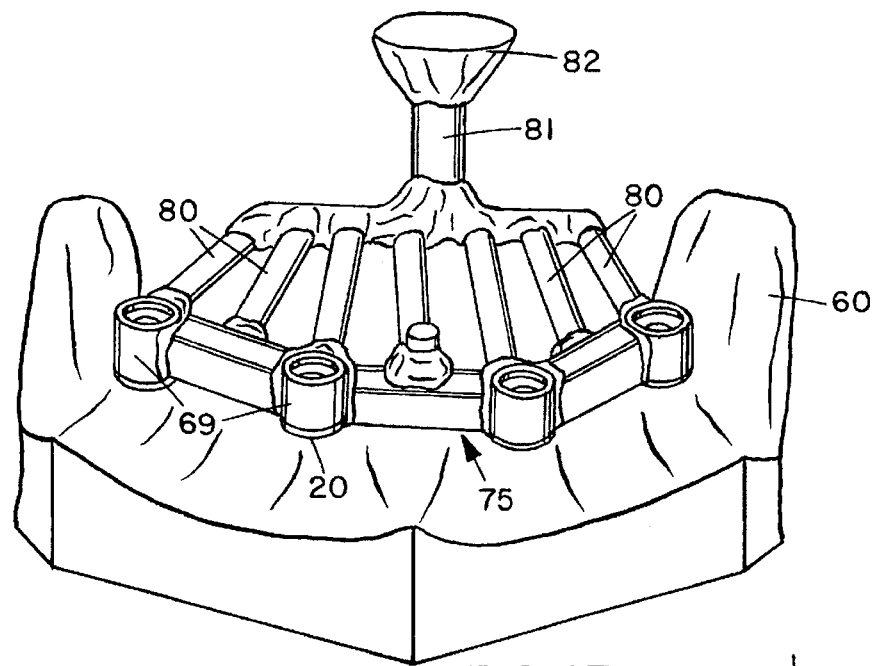
FIG. 15 is a similar view with casting sprues added.
Figure 16:
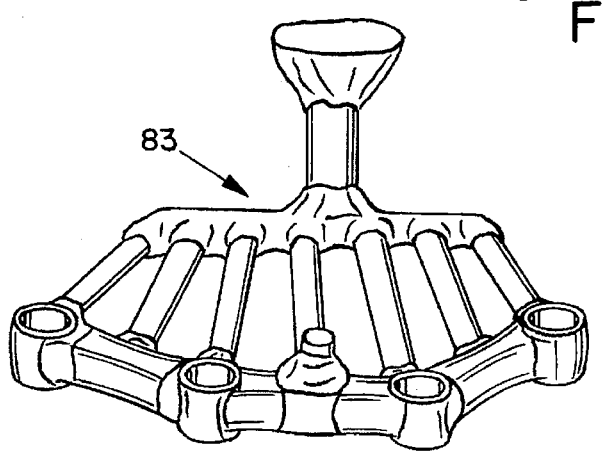
FIG. 16 illustrates the bar model with final shaping ready for making a mold for casting.

After verification and any necessary adjustments, the verified plastic bar pattern is returned to the laboratory for casting. The plastic bar pattern 75 is again secured to the model and checked for a proper fit. Sprues 80 are run to the thickest parts of the bar pattern, using 10 or 12 gauge sprue wax. Sprues are preferably also attached to the top of each of the castable sleeves, as illustrated in FIG. 15. The sprues are set at a 45° angle, and are each secured to a central sprue chimney 81 having an inlet nozzle 82. The resultant sprued plastic bar pattern is then removed from the model. Final shaping is performed on the sprued pattern prior to making a mold using the pattern. The finally shaped pattern 83 prior to making the mold is illustrated in FIG. 16.

The wax and plastic pattern is used in an investment casting process to form a high precision mold in a casting ring. The investment casting material is poured into the ring, making sure the material completely fills the interior of each casting sleeve. The invested bar pattern is placed into a furnace and the furnace temperature is raised until a temperature is reached at which the plastic and wax will be burnt out. The resultant mold is used to cast the bar. Precious or semi-precious alloys, such as yellow gold, white gold, silver and palladium alloys, are used to make the cast bar. Base metal alloys should not be used. The bar is then cast into the mold.

Once the cast bar has hardened and bonded to the precious metal seats and to the stainless steel socket members, the mold is divested. Care is taken when divesting so as not to damage the machined gold seats on the undersurface of the bar. To remove the carbon rod from each cast-to female socket, it is broken off and the socket is blasted with glass beads to eliminate the remainder of the carbon. A reamer is used on the internal bore of each cast sleeve or through bore to remove any casting imperfections and to clear the inside seat for receiving the female member 26. The sprues are cut off and the bar is polished. A bar polishing cap (not illustrated) is provided to protect the machined gold seats from damage during finishing and polishing procedures. Each polishing cap is fastened to the bottom of a respective gold seat by a female attachment screw or member 26.

A final fit of the finished bar is made on the laboratory model, and the finished cast bar and attachment screws are delivered to the dental office for fitting to the patient. The bar is then secured in the oral cavity using the appropriate attachment female members 26 and retaining screws 50. The fit is verified. Once placement of the bar is completed, an impression male member is snapped into each female socket, either in socket members 26 or into sockets 13 cast into the bar. The cast bar must be finished down level with the upper face of the female member 26, to ensure that the male can be completely seated into the female socket. An impression is then taken for making the prosthesis. A female analog is snapped onto each impression male in the impression, and a master cast is poured which will replicate the position of the bar and each female socket in the patient's mouth.

A standard male 24 with an attached cap 25 is then snapped into each female analog in the master cast, while the centering ring 46 ensuring each male is axially aligned with the desired path of insertion. The prosthetic appliance is then processed. The centering sleeve or ring 46 is then removed. Centering sleeve 46 seats in the flared inlet opening 37 of the female socket to ensure proper centering of the male part during processing of the denture. The denture can then be snapped into the patient's mouth easily simply by snapping the end of each male into the appropriate bar or female socket.

The snap-in, nylon male members will deteriorate over time so that retention of the snap fit gradually diminishes. Typically, after one to three years of use, the nylon male members must be replaced. This may be accomplished relatively easily. A suitable coring tool is used to core out the male post from the cap. A blade or explorer-like instrument is then used to remove the remaining plastic ring from the metal cap which is bonded in the denture. At this point, the head 42 of a replacement male member 24 may be pushed into the metal denture cap until it is seated securely in place.

The low profile, implant bar attachment system of this invention is simpler and causes less stress or damaging torquing forces on implants than previous bar systems. By providing sockets in the bar itself and corresponding male members on the denture which snap down into the bar, the height of the bar above the gum line is reduced considerably. The connection point for the prosthesis is thus provided low within the bar. The cap 25 is short and strong, and takes up very little vertical height above the cast bar. The implant bar system measures only about 4.5 mm to 5 mm from the tissue to the top of the male cap. This means that it is 25% or more shorter than previous bar systems.

Additionally, by attaching the denture to the bar at the implant sites, rather than at locations offset to one side of the implant sites, as in prior systems, forces are directed along the longitudinal axis of the implant itself, rather than distally. This provides safe axial loading on the implants, and avoids cantilever or torquing forces which can damage or loosen implants. The resilient nylon male member and the 360° ball and socket rotation permitted between the male member and female socket further reduce stress on the supporting implants. The system is compatible with all major implant designs.

The use of a castable plastic bar pattern in an investment casting technique to make the cast bar virtually eliminates the inconvenience of cut and solder corrections on fitting to the patient. The castable plastic pattern can be readily fitted in the patient's mouth prior to casting, and any necessary corrections may be made easily simply by cutting and re-bonding the plastic bar. This insures a perfect final fit of the cast bar in the majority of cases, with no cutting or soldering required.

The plastic bar pattern preferably includes machined gold seats wherever the bar meets an implant or implant abutment. This means that the same precision fit is being evaluated before and after the casting. The machined gold seats insure a precise, close fit to the mating face of the implant or implant abutment, both before and after casting. The cost of the purer gold material used for the seats makes it too expensive to use this material for the entire bar. However, by using this material in the seating areas, a precise fit is insured at the most critical point in the attachment system.

Another advantage of providing sockets for snap engagement with male members at the actual implant sites is that attachment points are readily available even where two implants are placed relatively close together. In prior systems, dentures could not be attached to bars in spaces between implants which were too close together. In this system, the spaces between implants do not have to be used for providing denture attachment points, since the denture is attached directly at the implant site.

Although a preferred embodiment of the invention has been described above by way of example only, it will be understood by those skilled in the field that modifications may be made to the disclosed embodiment without departing from the scope of the invention, which is defined by the appended claims.

We claim:

1. A dental implant bar system, comprising:
    an elongate bar for extending between at least two dental implants, the bar having an upper face facing away from the implants and a lower face facing the implants;
    at least two fastener devices for connecting the bar to the respective dental implants;
    at least two socket formations with a low profile within the bar and having openings in the upper face of the bar, each socket formation comprising first snap engagement means; and
    at least two male members, each male member comprising an elongate shaft having a first end for securing in a dental appliance and a second end comprising an enlarged head, the enlarged head comprising second snap engagement means for releasable snap engagement through one of said openings into a respective one of said socket formations.

2. The system as claimed in claim 1, wherein the bar has at least two through bores, each through bore being aligned with the location of a respective one of said implants, and said fastener devices each have a head for engagement in said through bore and a shaft for projecting through said bore out of the lower face of said bar for securing to a respective implant.

3. The system as claimed in claim 2, wherein the head of at least one of said fastener devices has a socket comprising one of said socket formations for snap engagement with the second end of one of said male members, whereby said appliance is secured to said bar at the same location as said implant for axial loading purposes.

4. The system as claimed in claim 3, wherein the head of both of said fastener devices has a socket, said sockets comprising said socket formations for snap engagement with the second ends of said respective male members.

5. The system as claimed in claim 3, wherein said socket has a lower end, and a tool receiving bore extends downwardly from the lower end of said socket into said shaft for receiving a tool for tightening or releasing said fastener device.

6. The system as claimed in claim 2, wherein each through bore is of stepped diameter, having a larger diameter upper portion and a smaller diameter lower portion, the head of each fastener device having a diameter substantially equal to said larger diameter for fitting into the larger diameter portion of a respective bore with the shaft projecting through the smaller diameter portion of the bore.

7. The system as claimed in claim 2, wherein the shaft of at least one fastener device is threaded for threaded engagement in a threaded bore of an implant.

8. The system as claimed in claim 2, including at least one abutment member having a cylindrical cuff for securing to the lower face of the bar between the bar and a respective implant in alignment with a respective one of said through bores, the cuff having an upper end, a lower end, a shaft of reduced diameter projecting from the lower end for connection to the implant, and a mating formation at the upper end for mating engagement with the shaft of a respective fastener device.

9. The system as claimed in claim 8, wherein the shaft of the respective fastener device is threaded, and the mating formation comprises a threaded bore projecting inwardly from the upper end of said cuff for mating engagement with said threaded shaft.

10. The system as claimed in claim 8, wherein the lower face of said bar at the respective through bore and the upper face of said cuff have matching shapes for mating engagement between said respective lower and upper faces when said fastener device is secured to said cuff.

11. The system as claimed in claim 8, including a plurality of abutment members having different cuff heights for selective attachment to said bar.

12. The system as claimed in claim 1, wherein at least one of said socket formations comprises a socket formed with a low profile within said bar at a location spaced from said fastener devices.

13. The system as claimed in claim 1, wherein the majority of said bar is of cast metal, said bar having through bores at least at opposite ends of said bar for alignment with respective implants, each fastener device having a head for engagement in said through bore and a shaft depending downwardly from said head and bar.

14. The system as claimed in claim 13, wherein said bar has a plurality of precision machined, annular metal seats secured to the lower surface of said bar at each through bore, each seat having a lower surface shaped for mating engagement with the upper surface of an implant.

15. The system as claimed in claim 14, including a plurality of abutment members for selective connection to said fastener devices at the lower face of said bar, each abutment member comprising a cylindrical cuff of predetermined height having an upper face for mating engagement with the lower surface of a respective seat, and a downwardly depending shaft for mating engagement with an implant, at least some of the abutment members having different cuff heights.

16. The system as claimed in claim 13, wherein each bore is of stepped diameter and has an upwardly facing step comprising a seat and said head has a downwardly facing seating surface for mating engagement with said seat.

17. The system as claimed in claim 16 wherein said seat and seating surface have matching tapered portions.

18. The system as claimed in claim 1, including at least two caps for securing in respective recesses in a dental appliance, each cap having a cap socket for snap locking engagement with the first head of said male member.

19. The system as claimed in claim 1, wherein said enlarged end is rotatable relative to said socket formation.

20. The system as claimed in claim 1, wherein the enlarged end and socket formation comprise a ball and socket connection.

21. The system as claimed in claim 1, wherein said bar is curved to follow the curvature of the jaw ridge, whereby support is provided directly under the dental appliance teeth where the forces of mastication are greatest.

22. The system as claimed in claim 1, wherein the bar has a plurality of through bores for alignment with a series of implants, and at least one offset portion having a divergent through bore for alignment with a divergent implant, and a retaining screw for extending through the divergent through bore to attach the bar to the divergent implant.

23. A method of making a bar for splinting together two implants and securing the implants to an overlying denture, comprising the steps of:
    taking an impression of the implant locations in a patient's jaw to which a denture is to be attached;
    using the impression, fabricating a model of the patient's jaw including implant analogs at the implant locations;
    securing a castable plastic sleeve to each implant analog;
    securing a castable plastic bar section between each adjacent pair of plastic sleeves to form a plastic framework;
    shaping the plastic bar framework to the desired jaw contour;
    fitting the plastic bar framework in the patient's jaw as a passive fit verification by fastening each sleeve to a respective implant and cutting and reshaping the bar if necessary for a correct fit; and
    using the plastic bar framework to cast a matching metal bar.

24. The method as claimed in claim 23, including the steps of securing a machined metal seat to the lower end of each plastic sleeve prior to securing the sleeve to an implant analog, the seat having a lower face of shape and dimensions for close mating engagement with the upper face of the implant analog.

25. The method as claimed in claim 23, wherein a castable plastic sleeve is secured to each implant analog using a fastener screw having a head of predetermined height, the fastener screw being selected from a plurality of fastener screws of differing heights depending on the crest height at the implant site.

26. The method as claimed in claim 25, including the steps of marking each sleeve at a height adjacent the upper end of the respective fastener screw, and cutting off the sleeve at the marked height, prior to securing the castable bar section between each pair of adjacent, cut off sleeves.

27. The method as claimed in claim 23, including the steps of forming at least one recess in an upper face of the plastic bar framework at a location between adjacent implant sites, and bonding a metal socket member in the recess with a bar secured to the socket member projecting upwardly from the bar in a direction parallel to the axes of at least the majority of the sleeves.

28. The method as claimed in claim 23, wherein all the sleeves have parallel central axes.

29. The method as claimed in claim 23, wherein at least one of the implant analogs is divergent from the other analogs by an angle of at least 10°, and one of the castable sleeves is secured to the divergent analog at a corresponding angle offset from the axes of the other castable sleeves.

30. The method as claimed in claim 23, including the step of using the plastic bar framework in an investment casting process to make a mold for casting a matching metal bar having a through bore at the site of each castable sleeve.

31. The method as claimed in claim 23, including the step of machining opposite ends of each plastic bar section to form a concave end surface for fitting against the cylindrical surface of a respective sleeve when the bar section is secured to the sleeve.

32. A method of attaching a denture to at least two implants in a patient's jaw, comprising the steps of:
    securing a bar to at least one implant at each end of the bar and at least one implant between the two end implants by means of fastener devices at each implant site, each fastener device having a head seated in a through bore in the bar at a respective implant site and a shaft projecting out of the bore for securing to an implant or implant abutment;
    the heads of at least the two fastener devices at opposite ends of the bar each having a socket formation;
    securing two male members to a denture, each male member being secured at a location corresponding to a respective one of the end implant attachment sites; and
    snap engaging the respective male members into the respective socket formations of the fastener devices to releasably secure the denture to the bar.

33. The method as claimed in claim 32, including the steps of measuring the gum thickness at each implant site, securing an abutment member of cuff height matching the gum thickness to an implant at each deep implant site where the gum thickness is greater than a predetermined thickness, securing the fastener devices to the respective abutment members at the deep implant sites, and securing the fastener devices directly to the implants at implant sites where the gum thickness is less than the predetermined thickness.

34. The method as claimed in claim 32, wherein the bar is secured to a plurality of implants, including the steps of determining whether any of the implants to which the bar is to be secured is divergent from the remaining implants and the desired path of prosthesis insertion by more than a predetermined angle, providing a correspondingly divergent through bore in the bar at any divergent implant, and securing the bar to the divergent implant by means of a retainer screw extending through the divergent through bore, the denture being provided with male members at all non-divergent implant sites.

35. The method as claimed in claim 34, including the step of providing a socket in the bar adjacent each divergent implant site, the socket being shaped for snap engagement with a male member, and securing a male member to the denture in alignment with the socket.

* * * * *